United States Patent [19]

Treybig et al.

[11] Patent Number: 4,783,327

[45] Date of Patent: Nov. 8, 1988

[54] SULFUR DIOXIDE REMOVAL FROM GAS STREAMS USING HYDROXYALKYL SUBSTITUTED PIPERAZINONES

[75] Inventors: Duane S. Treybig; James L. Potter; Mark B. Jones; John M. Motes, all of Lake Jackson, Tex.

[73] Assignee: The Dow Chemical Company, Midland, Mich.

[21] Appl. No.: 85,432

[22] Filed: Aug. 13, 1987

[51] Int. Cl.[4] .................. C01B 17/00; B01D 19/00
[52] U.S. Cl. .................................... 423/243; 55/73
[58] Field of Search ............... 423/242 A, 242 R, 243; 55/73

[56] References Cited

U.S. PATENT DOCUMENTS

| 4,112,049 | 9/1978 | Bozzelli et al. | 423/243 |
|---|---|---|---|
| 4,366,134 | 12/1982 | Koroay et al. | 423/243 |
| 4,465,614 | 8/1984 | Trentham et al. | 252/364 |
| 4,469,663 | 9/1984 | Crump et al. | 423/242 |
| 4,530,704 | 7/1985 | Jones | 55/48 |

*Primary Examiner*—Gregory A. Heller
*Attorney, Agent, or Firm*—A. Cooper Ancona

[57] ABSTRACT

A method of removing $SO_2$ from a gas stream containing the same by absorbing the $SO_2$ in an aqueous solution containing a 4-(2-hydroxyalkyl)-2-piperazinone compound or an alkyl or aryl substituted derivative thereof. These compounds provide an absorbent solution which is less subject to loss during the regeneration step and yet effectively remove the $SO_2$ from the gas stream without interference from other associated gases.

18 Claims, No Drawings

SULFUR DIOXIDE REMOVAL FROM GAS STREAMS USING HYDROXYALKYL SUBSTITUTED PIPERAZINONES

BACKGROUND OF THE INVENTION

The removal of sulfur-containing gases from gas streams is important in the purification of natural gas before burning it for home and industrial use and in the clean up of flue gases used in coal-burning industries. One process still widely used today employs the well known limestone scrubbing. The disadvantage of this process is the necessity of disposing of the large volume of solid waste produced. Many compounds have been suggested as absorbents, some of which are selective to $H_2S$ or $CO_2$. Others are capable of removing a large percent of all the acidic gases present in the gas stream being treated. One system taught in a recent patent, U.S. Pat. No. 4,366,134, employs potassium or sodium citrate to selectively remove $SO_2$ from a gas stream. In another more recent patent, U.S. Pat. No. 4,530,704, the removal of $SO_2$ from a gas stream is accomplished by contacting a gas stream containing it with an aqueous solution of a piperazinone, morpholinone or their N-alkyl substituted derivatives, eg N,N'-dimethyl-2-piperazinone. Each of the compounds employed by the above patents can be regenerated by the conventional method of steam stripping.

An improved method for absorbing $SO_2$ from gas streams has now been discovered wherein hydroxyalkyl-2-piperazinones are employed as absorbents.

SUMMARY OF THE INVENTION

The present invention is a method for removing $SO_2$ from a gas stream containing it, and which may also contain other gases commonly associated with hydrocarbon streams or combustion gases, by employing as an absorbent therefor an aqueous solution of an N-hydroxyalkyl-2-piperazinone or an alkyl or aryl substituted derivative thereof.

DETAILED DESCRIPTION OF THE INVENTION

The compounds useful as absorbents for removing $SO_2$ from gas streams are 4-(2-hydroxyalkyl)-2-piperazinones having the formula:

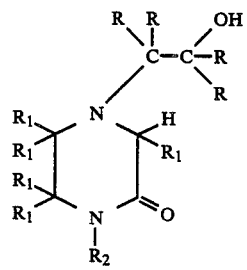

wherein R is hydrogen or an alkyl group having 1 or 2 carbon atoms, $R_1$ is hydrogen, an alkyl group having 1 to 6 carbon atoms or an aryl or an aralkyl group having from 6 to 12 carbon atoms and $R_2$ is hydrogen, an alkyl or hydroxyalkyl group having from 1 to 6 carbon atoms or an aryl or aralkyl group having from 6 to 12 carbon atoms.

Suitable 4-(2-hydroxyalkyl)-2-piperazinones include 4-(2-hydroxyethyl)-2-piperazinone, 4-(2-hydroxyethyl)-1-methyl-2-piperazinone, 4-(2-hydroxyethyl)-3-methyl-2-piperazinone, 4-(2-hydroxyethyl)-5-methyl-2-piperazinone, 3-ethyl-4-(2-hydroxyethyl)-2-piperazinone, 3-ethyl-4(2-hydroxyethyl)-2-piperazinone, 6-ethyl-4-(2-hydroxethyl)-2-piperazinone, 4-(2-hydroxyethyl)-5,6-dimethyl-2-piperazinone, 1-ethyl-4-(2-hydroxyethyl)-2-piperazinone, 4-(2-hydroxyethyl)-3-phenyl-2-piperazinone, 1,4-bis(2-hydroxyethyl)-2-piperazinone, 4-(2-hydroxypropyl)-2-piperazinone, 4-(2-hydroxybutyl)-2-piperazinone and 4-(2-hydroxypropyl)-6-methyl-2-piperazinone.

High boiling absorbents are desirable to prevent loss of the absorbent along with the $SO_2$ during the regeneration step. The subject compounds possess a much higher boiling point than the N,N'-dialkyl-2-piperazinones employed for that purpose in U.S. Pat. No. 4,530,704. For example, while N,N'-dimethyl-2-piperazinone boils at 241° C., 4-(2-hydroxyethyl)-2-piperazinone boils at 450° C., both at atmospheric pressure. The higher boiling point is thought to be due to the formation of a dimer during heating which, of course, occurs during the regeneration step.

The compounds of the present invention are employed in aqueous solution at a concentration of from about 0.1 molar up to about their saturation concentration in water. The absorbent solution, after use, is thermally regenerated, eg. by passing steam through the solution, and recycled to the absorption step. The absorber can be operated at a temperature of from about 0° to about 120° C., but is preferably operated at a temperature of from about 5° to about 95° C.

Pressures of from about atmospheric to about 3 atmospheres can be employed but atmospheric pressure is preferably and conveniently employed. Higher temperatures and pressures are not deleterious, but equipment design modifications may be required.

The $SO_2$ concentration of the gas streams being treated may vary from about ten ppm up to 45 vol.%.

Preparation of the compounds useful in the invention is accomplished by reacting the appropriate 2-piperazinone or substituted derivative thereof with ethylene oxide or ethylene chlorohydrin. An improved method of preparation involves the reaction of an N-hydroxyalkylalkylenediamine with glyoxal or a substituted glyoxal. Details of this process are disclosed in a co-filed application of two of the inventors of the present application entitled "PREPARATION OF HYDROXYALKYLPIPERAZINONES BY REACTING GLYOXAL WITH HYDROXYALKYLDIAMINES", Ser. No. 085,428 filed Aug. 13, 1987, and is incorporated herein by reference in-so-far as the making of compounds useful in the process of the present invention is concerned.

The following examples illustrate the use of the absorbents in the process of the invention.

EXAMPLE 1

The product of the reaction of 30% aqueous glyoxal solution with 70% aqueous 2[(2-aminoethyl)amino]ethanol is concentrated in a rotary evaporator under full vacuum at a temperature of 100° C. The resulting product (75% 4-(2-hydroxyethyl)2-piperazinone) is distilled under vacuum. The yellowish-brown liquid distillate is dissolved in 1-propanol and a water-propanol azeotrope removed by distillation at 70° C. at a final pressure of <5 mm Hg. The product is dissolved in acetonitrile solution, then precipitated by chilling to 4° C., filtered and finally crystallized from acetone to obtain a white product (mp 59.5°–60° C., bp 450° C.). Capillary gas chromatography indicates the white crystalline solid is 99+% pure 4-(2-hydroxyethyl)-2-piperazinone.

EXAMPLE 2

An aqueous solution of 10 wt% of the 4-(2-hydroxyethyl)-2-piperazinone (HEP) prepared in Example 1 is evaluated as a selective solvent for absorption and regeneration of sulfur dioxide. In order to demonstrate that 4-(2-hydroxyethyl)-2-piperazinone could be recycled three times, $SO_2$ from a synthetic gas mixture is absorbed with the same aqueous solution of HEP and then regenerated. The procedure used is that described in U.S. Pat. No. 4,530,704, which is incorporated herein by reference. The synthetic gas mixture consists of approximately 77% nitrogen, 20% carbon dioxide and 3% sulfur dioxide. The synthetic gas mixture is fed into the bottom of a ten-tray Oldershaw column between 30° to 35° C. and at about 4.9 mL/min. The aqueous solution of the absorbent is fed into the top of the column at a rate of 5 mL/min. The operating conditions of the absorber column for the 10 wt.% aqueous solution of HEP during the three cycles, the specific composition of the synthetic gas mixture and the analysis of the gas composition after leaving the column are summarized in Table I. HEP absorbs nearly 100% of the $SO_2$ from the gas stream in all three cycles.

stripped for the three cycles are summarized in Table II. Seventy-two to seventy-nine percent of the $SO_2$ absorbed by the HEP solution is stripped. Also, the HEP solution maintains its absorption and regeneration efficiency throughout 3 cycles.

TABLE II

| | | | \multicolumn{3}{c|}{$SO_2$ REGENERATION FROM HEP ABSORBENT} | | | |
|---|---|---|---|---|---|---|---|---|
| | | | | Temperature (°C.) | | Wt % $SO_2$ | | |
| Cycle No | Feed Rate (mL/min) | Pressure (mm Hg) | Preheat | Bottom of Column | Overhead | Liquid In | Liquid Out | % $SO_2$ Stripped |
| 1 | 4 | 1 | 78 | 98 | 99 | 3.20 | 0.91 | 72 |
| 2 | 4 | 1 | 77 | 99 | 99 | 4.22 | 0.88 | 79 |
| 3 | 4 | 1 | 75 | 98 | 99 | 4.24 | 1.00 | 76 |

EXAMPLE 3

An aqueous solution of 20 wt% glyoxal is added dropwise over a 3 hour period to an aqueous solution of 30 wt% 2-[(2-aminoethyl)amino]ethanol at 100° C. The hot aqueous reaction mixture is treated with charcoal (NORIT A), filtered and vacuum stripped. Capillary gas chromatography indicates the golden product is 90% pure 4-(2-hydroxyethyl)-2-piperazinone.

EXAMPLE 4

An aqueous solution of 10 wt% of the HEP prepared in Example 3 is evaluated as a selective solvent for absorption and regeneration of sulfur dioxide. Four times, $SO_2$ from a synthetic gas mixture is absorbed with the same aqueous solution of HEP and then regenerated to demonstrate that HEP can be recycled. The composition of the synthetic gas mixture and operating conditions for the absorber and stripper systems are nearly the same as that employed in Example 2. The operating conditions of the absorber column for the aqueous solution of HEP, the specific composition of the synthetic

TABLE I

| | | | \multicolumn{2}{c|}{$SO_2$ ABSORPTION WITH HEP} | | | | | | |
|---|---|---|---|---|---|---|---|---|---|---|
| | | | \multicolumn{3}{c|}{Temperature (°C.)} | | | | | | |
| Cycle No. | Gas Rate (Liters/min) | Pressure (mm Hg) | Preheat | Bottom of Column | Top of Column | \multicolumn{3}{c|}{Wt % Gas In} | \multicolumn{3}{c}{Wt % Gas Out} |
| | | | | | | $N_2$ | $CO_2$ | $SO_2$ | $N_2$ | $CO_2$ | $SO_2$ |
| 1 | 4.90 | 35 | 77 | 31 | 52 | 76.94 | 19.93 | 3.13 | 79.0 | 21.10 | 0 |
| 2 | 4.95 | 32 | 80 | 35 | 54 | 77.30 | 19.59 | 3.11 | 79.70 | 20.29 | 0.005 |
| 3 | 4.93 | 36 | 78 | 30 | 50 | 77.54 | 19.46 | 2.99 | 79.76 | 20.24 | 0.004 |

The aqueous solution of the HEP is preheated to between 75° and 78° C. and then passes through a stripper column. The aqueous solution of the absorbent is fed at the top of the column at a rate of 4 mL/min. under a pressure of 1 mm Hg. The temperature of the liquid at the top of the column and at the bottom of the column is either 98° or 99° C. The steam stripped $SO_2$ exits the top with some water vapor. The lean absorbent exits the bottom of the stripper column. The operating conditions of the stripper column for the HEP, the weight % $SO_2$ entering the column and exiting with the absorbent out the bottom of the column and the % $SO_2$ gas mixture and the analysis of the gas composition leaving the column is summarized in Table III. The HEP absorbed nearly 100% of the $SO_2$ from the synthetic gas stream in all four cycles.

The operating conditions of the stripper column containing the HEP, the weight % $SO_2$ entering the column and the % $SO_2$ stripped for the four cycles is given in Table IV. Seventy-four to seventy-eight percent of the $SO_2$ absorbed by the HEP solution was stripped. The HEP solution maintains its absorption and regeneration efficiency throughout four cycles.

TABLE III

| | | | | \multicolumn{2}{c|}{$SO_2$ ABSORPTION WITH HEP} | | | | | | |
|---|---|---|---|---|---|---|---|---|---|---|---|
| | | | | \multicolumn{3}{c|}{Temperature (°C.)} | | | | | | |
| Cycle No. | Feed Rate (mL/min) | Gas Rate (Liters/min) | Pressure (mm Hg) | Preheat | Bottom of Column | Top of Column | \multicolumn{3}{c|}{Wt % Gas In} | \multicolumn{3}{c}{Wt % Gas Out} |
| | | | | | | | $N_2$ | $CO_2$ | $SO_2$ | $N_2$ | $CO_2$ | $SO_2$ |
| 1 | 5 | 4.90 | 35 | 80 | 32 | 50 | 76.24 | 20.50 | 3.26 | 78.28 | 21.72 | 0 |
| 2 | 5 | 4.91 | 34 | 80 | 35 | 53 | 76.79 | 20.53 | 2.68 | 79.07 | 20.93 | 0.002 |
| 3 | 5 | 4.92 | 35 | 80 | 34 | 50 | 77.01 | 20.40 | 2.59 | 79.24 | 20.75 | 0.006 |

TABLE III-continued

SO₂ ABSORPTION WITH HEP

| Cycle No. | Feed Rate (mL/min) | Gas Rate (Liters/min) | Pressure (mm Hg) | Temperature (°C.) Preheat | Temperature (°C.) Bottom of Column | Temperature (°C.) Top of Column | Wt % Gas In $N_2$ | Wt % Gas In $CO_2$ | Wt % Gas In $SO_2$ | Wt % Gas Out $N_2$ | Wt % Gas Out $CO_2$ | Wt % Gas Out $SO_2$ |
|---|---|---|---|---|---|---|---|---|---|---|---|---|
| 4 | 5 | 4.93 | 34 | 80 | 34 | 52 | 76.81 | 20.73 | 2.46 | 78.85 | 21.14 | 0.006 |

TABLE IV

SO₂ REGENERATION FROM HEP ABSORBENT

| Cycle No | Feed Rate (mL/min) | Pressure (mm Hg) | Temperature (°C.) Preheat | Temperature (°C.) Bottom of Column | Temperature (°C.) Overhead | Wt % $SO_2$ Liquid In | Wt % $SO_2$ Liquid Out | % $SO_2$ Stripped |
|---|---|---|---|---|---|---|---|---|
| 1 | 4 | 1 | 77 | 99 | 99 | 3.85 | 0.88 | 77 |
| 2 | 4 | 1 | 76 | 99 | 99 | 4.70 | 1.05 | 78 |
| 3 | 4 | 1 | 76 | 99 | 99 | 4.69 | 1.08 | 77 |
| 4 | 4 | 1 | 75 | 99 | 99 | 4.74 | 1.22 | 74 |

COMPARATIVE EXAMPLE A

An aqueous solution of 10 wt% N,N'-dimethyl-2-piperazinone (NNDP) is evaluated as a selective solvent for absorption and regeneration of sulfur dioxide. The composition of the synthetic gas mixture and operating conditions for the absorber and stripper systems are substantially the same as those employed in Examples 2 and 4. The operating conditions of the absorber column for the aqueous solution of NNDP, the specific composition of the synthetic gas mixture and the analysis of the gas composition after leaving the column are summarized in Table V. The NNDP absorbed 100% of the $SO_2$ from the synthetic gas stream.

The operating conditions of the stripper column for the NNDP, the weight % $SO_2$ entering the column and the % $SO_2$ leaving the column is given in Table VI. Only sixty percent of the $SO_2$ absorbed by the NNDP solution was stripped.

TABLE V

SO₂ ABSORPTION WITH NNDP

| Feed Rate (mL/min) | Gas Rate (Liters/min) | Pressure (mm Hg) | Temperature (°C.) Preheat | Temperature (°C.) Bottom of Column | Temperature (°C.) Top of Column | Wt % Gas In $N_2$ | Wt % Gas In $CO_2$ | Wt % Gas In $SO_2$ | Wt % Gas Out $N_2$ | Wt % Gas Out $CO_2$ | Wt % Gas Out $SO_2$ |
|---|---|---|---|---|---|---|---|---|---|---|---|
| 5 | 4.96 | 35 | 80 | 35 | 57 | 76.76 | 19.86 | 3.38 | 79.42 | 20.57 | 0.0002 |

TABLE VI

SO₂ REGENERATION FROM NNDP ABSORBENT

| Feed Rate (mL/min) | Pressure (mm Hg) | Temperature (°C.) Preheat | Temperature (°C.) Bottom of Column | Temperature (°C.) Overhead | Wt % $SO_2$ Liquid In | Wt % $SO_2$ Liquid Out |
|---|---|---|---|---|---|---|
| 4 | 1 | 76 | 99 | 100 | 3.66 | 1.44 |

We claim:

1. In a method for removing sulfur dioxide from gas streams containing the same which comprises (a) contacting said stream with an aqueous solution of an absorbent for said sulfur dioxide, (b) subsequently thermally desorbing said sulfur dioxide and (c) recovering said sulfur dioxide, the improvement which comprises employing as the absorbent a compound having the formula

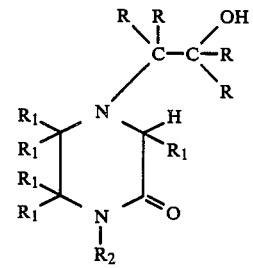

wherein R is hydrogen or an alkyl group having 1 or 2 carbon atoms, $R_1$ is hydrogen, an alkyl group having 1 to 6 carbon atoms or an aryl or an aralkyl group having from 6 to 12 carbon atoms and $R_2$ is hydrogen, an alkyl or hydroxyalkyl group having from 1 to 6 carbon atoms or an aryl or aralkyl group having from 6 to 12 carbon atoms.

2. The process of claim 1 wherein R is hydrogen.
3. The process of claim 2 wherein $R_1$ is hydrogen.
4. The process of claim 3 wherein $R_2$ is hydrogen.
5. The process of claim 3 wherein $R_2$ is an alkyl group.
6. The process of claim 5 wherein the alkyl group is methyl or ethyl.
7. The process of claim 3 wherein $R_2$ is a hydroxyalkyl group.
8. The process of claim 7 wherein the hydroxyalkyl group is hydroxyethyl.
9. The process of claim 2 wherein at least one $R_1$ is an alkyl group.
10. The process of claim 9 wherein the alkyl group is methyl or ethyl.
11. The process of claim 9 wherein $R_2$ is hydrogen.
12. The process of claim 10 wherein $R_2$ is hydrogen.
13. The process of claim 1 wherein the aqueous solution contains a concentration of the absorbent compound of at least about 0.1 molar.

14. The process of claim 4 wherein the aqueous solution contains a concentration of the absorbent compound of at least about 0.1 molar.

15. The process of claim 13 wherein the absorption of the $SO_2$ from the gas stream is conducted at a temperature of from about 0° to about 120° C.

16. The process of claim 14 wherein the absorption of the $SO_2$ from the gas stream is conducted at a temperature of from about 5° to about 95° C.

17. The process of claim 15 wherein the concentration of $SO_2$ in the gas stream is from about 10 ppm up to about 45 vol.% of the gas.

18. The process of claim 16 wherein the concentration of $SO_2$ in the gas stream is from about 10 ppm up to about 45 vol.% of the gas.

* * * * *